(12) United States Patent
Scandurra et al.

(10) Patent No.: US 6,673,839 B1
(45) Date of Patent: Jan. 6, 2004

(54) PHARMACEUTICAL COMPOSITIONS WITH ANTITUMOUR ACTIVITY

(75) Inventors: Laura Scandurra, Catania (IT); Franca Maria Stivala, Catania (IT); Eugenia Allegra, Catania (IT); Grazia Rapisarda, Catania (IT)

(73) Assignee: Universita' Degli Studi di Catania, Catania (IT)

( * ) Notice: Subject to any disclaimer, the term of this patent is extended or adjusted under 35 U.S.C. 154(b) by 0 days.

(21) Appl. No.: 09/806,153

(22) PCT Filed: Sep. 27, 1999

(86) PCT No.: PCT/EP99/07170

§ 371 (c)(1), (2), (4) Date: May 10, 2001

(87) PCT Pub. No.: WO00/18385

PCT Pub. Date: Apr. 6, 2000

(30) Foreign Application Priority Data

Sep. 30, 1998 (IT) .......................................... MI98A2090

(51) Int. Cl.[7] .................... A61K 31/195; A61K 31/205; A61K 31/215
(52) U.S. Cl. ....................... 514/556; 514/547; 514/533; 514/16; 530/311
(58) Field of Search ................................. 514/556, 547, 514/533, 16; 530/311

(56) References Cited

U.S. PATENT DOCUMENTS 5,504,069 A * 4/1996 Bogden et al. ................ 514/14

FOREIGN PATENT DOCUMENTS

| EP | 0 845 265 | 6/1998 |
|---|---|---|
| JP | 05-339148 | 12/1993 |
| WO | WO 97/05862 | 2/1997 |
| WO | WO 97/06788 | 2/1997 |
| WO | WO 97/34596 | 9/1997 |

OTHER PUBLICATIONS

Fischer et al. Toxicology in Vitro 3, 195–199 (1989).*
W.D. Thomitzek et al., "Die Wirkung von Palmitoylcarnitin auf Atmung, Glykolyse und Wachstum von Ehrlich–Ascites–Tumorzellen", *Die naturwissenschaften*, vol. 52, No. 23, Dec. 1965, pp 644–645.
W.D. Thomitzek et al., "Der Einfluss von Palmitoylcarnitin auf Ehrlich–Aszites–Tumorzellen in vitro und in vivo", *Acta Biol Med Ger*, vol. 17, No. 2, 1966, pp 145–159.
G. Vescovi et al., "Modulation by palmitoyl–carnitine of calcium activated phospholipid–dependent protein kinase activity and inhibition of melanoma cell growth", *The British Journal of Dermatology*, vol. 119, No. 2, 1988, pp 171–178.
Toshio Nakaki et al., "Inhibition by palmitoylcarnitine of adhesion and morphological change in HL–60 cells induced by 12–0–tetradecanoylphorbol–13–acetate", *Cancer Research*, vol. 44, No. 5, pp. 1908–1912, (1984).
K. Satyamoorthy et al., "Inhibition of mouse skin tumor promotion by adriamycin and daunomycin in combination with verapamil or palmitoylcarnitine", *Cancer Letters*, vol. 55, No. 2, pp 135–142 (1990).
B. Neri et al., "Differences between carnitine derivatives and coenzyme Q10 in preventing in vitro doxorubicin–related cardiac damages", *Onocology*, vol. 45, No. 3, 1988, pp. 242–246.
D. Krier et al., "Inhibition of Tumor Growth by L Carnitine", *74th Annual Meeting of the American Society of Biological Chemists*, vol. 42, o. 7, Jun. 1983.

* cited by examiner

Primary Examiner—Christopher S. F. Low
Assistant Examiner—Chih-Min Kam
(74) Attorney, Agent, or Firm—Young & Thompson

(57) ABSTRACT

Acylcarnitines, such as L-acetylcarnitine (I) were found to have marked antitumour activity, which can be further increased by simultaneous administration of somatosstatin.

4 Claims, No Drawings

PHARMACEUTICAL COMPOSITIONS WITH ANTITUMOUR ACTIVITY

This application is a 371 of PCT/EP99/07170, filed Sep. 27, 1999.

The present invention relates to pharmaceutical compositions with antitumour activity, containing as active ingredient one or more acylcarnitines optionally in combination with other substances with antitumour activity. In particular, the invention relates to pharmaceutical compositions with antitumour activity, containing as active ingredient L-acetylcarnitine optionally in combination with somatostatin. The invention further relates to the use of acylcarnitines, in particular L-acetylcarnitine, for the preparation of medicaments with antitumour activity. Carnitines (which herein means carnitine, as well as the acylderivatives, optical isomers and racemates thereof) are compounds naturally occurring in various organs and systems of a number of living species, both vegetables and animals. Such compounds are available in the synthetic form, and they are used in common clinical practice in the treatment of primary carnitine deficiency, senile dementia and peripheral neuropathies. The recommended dosage for use in humans is about 30/mg/kg/day.

More particularly, acylcarnitines show a number of therapeutical properties, in that they have immunomodulating, antibacterial, antifungal, antishock, antidyslipidemic activities. Furthermore, they have a remarkable antiviral activity.

It has now been surprisingly found that acylcarnitines have a remarkable antitumour activity.

It has, for example, been observed that acetylcarnitine (N,N,N,-trimethyl-β-acetoxy-butyrobetaine), of formula

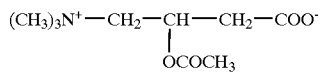

mainly in its L form, has a strong antitumour activity, both in animals and in humans and can therefore be used, either alone or in combination with other antitumour medicaments, in the treatment of malignant tumours.

Pre-treatment with acylcarnitine, in particular with L-acetylcarnitine, has been found to prevent the thriving of transplanted neoplasms in the animals and the relapses of resected neoplasms in humans.

The results obtained with L-acetylcarnitine hydrochloride, which will hereinafter referred to as L-aC, are reported in the following by way of example. It should, however, be taken into account that such antitumour activity is not restricted to L-aC, but is also shown by other acylcarnitines having an acyl residue containing 3 to 18 carbon atoms and that the corresponding racemic forms also show said activity, although to a lesser extent.

Experimental Evidence

The studies carried out to prove the antitumour activity exerted by L-aC, according to the present invention, can be summarized as follows:

1. Effects of L-aC on Cultured Primitive Human Tumour Cells

The effects of L-aC on cells from 4 primitive epidermoid carcinomas of the larynx and 1 primitive undifferentiated carcinoma of the nasopharynx were tested.

Tissue fragments from the tumour mass were mechanically dissociated in Hank's solutions adding an antibiotic and an antifungal to obtain a cell monosuspension free of agglomerates. The resulting suspension was centrifuged at 1200 rpm for 5 m' and the pellet was resuspended in MEM culture medium supplemented with 10% of patient serum, to obtain a concentration of $2-3\times10^4$ cells/ml of medium. 1 ml Samples were prepared from the suspension, in amounts equivalent to the number of the concentrations to be assayed (0.2–20 mg/ml) as well as a control sample.

The suspensions were exposed to the medicament in Dubnoff bath at 37° C. for 24 h, then centrifuged and resuspended in 1 ml of fixing solution (tris buffer+methanol (1:3)) for 30 minutes and finally stained with 0.5% propyl iodide with simultaneous treatment with RNase.

Cytofluorimetric analysis in order to evaluate the percentage distribution of the cell cycle phases, was performed by an Ortho Diagnostic Spectrum III cytofluorigraph, equipped with Graphic Method computerized program.

The evaluation of the cell sensitivity to the medicament was based on the extent of the perturbations induced by L-aC on the cell cycle.

L-aC at a concentration of 0.2 mg/ml proved to exert on all the samples an activity slightly promoting the S phase, inducing an about 10% increase in the percentage of S phase cells compared with the control.

L-aC at a concentration of 20 mg/ml caused a block in the percentage of the cells in $G_1$ phase, with the inversion of the $G_1/S+G_2M$ ratio compared with the control. In particular, a tumour with a pre-treatment $G_1/S+G_2M$ ratio of 31/69 showed, after the treatment, a 70/30 ratio.

2. Effects of L-aC on Cultured Secondary Human Tumour Cells

L-aC was tested on tumour cells from lymph nodes taken from the same patients from which the primitive neoplasms had been taken.

The activity of L-aC on tumour cells from said lymph nodes, at a concentration of 20 mg/ml, was comparable, in all samples, to that exerted at the same concentration on cells from the primitive tumours.

In particular, a tumour with a pre-treatment $G_1/S+G_2M$ ratio of 20/80 showed, after treatment, a 74/26 ratio.

The studies of point 1 and 2 evidence that L-aC, administered at a concentration of 20 mg/ml, is able to impact "in vitro" on the cell cycle of tumour cells, inducing a marked block in $G_1$, thus remarkably inhibiting cell replication and tumour progression.

3. Effects of L-aC on Stabilized Human Neoplastic Cell Lines

The effects of L-aC on stabilized human neoplastic cell lines were tested using the methylene blue assay.

Acute promyelocytic leukemia cell line (HL60) and prostate (Du 145), colon (HT 29) and breast (MCF 7) adenocarcinoma cell lines have been used.

Cell suspensions at concentrations of $10^5$ cells/ml were prepared.

100 μl of the obtained cell suspension were inoculated on 96 well plates and incubated at 37° for 12 hours, to obtain cell adhesion to the plates. After 12 hours, L-aC was added at the concentrations of 0.2 mg/ml, 2 mg/ml, 20 mg/ml. After 72 hours, the culture medium was removed and 100 μl of 100% ethanol were added for 30 min. Subsequently ethanol was removed and 1% methylene-blue was added for 2 hours. The dye was then removed and the plates were dried before adding 1M HCl.

The cytotoxicity percentage was calculated using the following formula:

$$(1-[O^D \text{ treated cells}/O^D \text{ control cells}]\times 100.$$

The optical density was evaluated by Uniskan microspectrophotometer with 630 nm wavelength filter.

Results

All the tested cell lines proved to be sensitive to L-aC activity, although with some differences.

Phenomena suggestive of programmed cell death were already observed at a L-aC concentration of 0.2 mg/ml, in all the assayed cell lines.

The induction of apoptosis has been detected due to nuclear cromatin condensation, cytoplasmic shrinking, endoplasmic reticulum dilatation and membrane blebbing together with DNA fragmentation.

Said phenomena were more marked and evident in the cells exposed to a L-aC concentration of 2 mg/ml.

The induction of apoptosis (appraised by Giemsa staining) was remarkable mainly on stabilized human neoplastic cell lines from breast and colon carcinomas.

In fact, cytotoxicity on these cell lines, i.e. the percentage of dead cells observed 48 hours after exposure to concentrations of L-aC of 20 mg/ml, was respectively 68% and 63%.

Cytotoxicities on stabilized human neoplastic cell lines from prostate carcinoma and acute promyelocytic leukemia were respectively 58% and 52%. No significant changes were observed in the L-aC concentration range from 2 to 20 mg/ml.

4. "In vitro" Short-term Chemosensitivity Assay

The effects of L-aC on cells from 4 primitive epidermoid carcinomas of the larynx and 1 primitive undifferentiated carcinoma of the nasopharynx were tested.

Tissue fragments from the tumour mass were mechanically dissociated in Hank's solutions adding an antibiotic and an antifungal to obtain a cell monosuspension free of agglomerates. The resulting suspension was centrifuged at 1200 rpm for 5 minutes and the pellet was resuspended in MEM culture medium supplemented with 10% of patient serum, to obtain a concentration of $10^5$ cells/ml. Subsequently, 180 $\mu$l of the resulting suspension were dispensed in microplate wells and incubated under 5% $CO_2$ atmosphere at 37° C. for 3 days. After that, the antitumor medicaments were added in the amount of 20 $\mu$l for each well, at a concentration of 0.1x, 1x and 10x the maximum serum concentrations that can usually be reached in clinical practice. 24 h after the beginning of the exposure to the antitumour medicament, 100 $\mu$l of MTT were added, and after 4 h, a further 150 $\mu$l of dimethylsulfoxide were added.

The optical density was evaluated by a Uniscan microspectrophotometer with a 550 mm wavelength filter. Cytotoxicity was evaluated as percentage of the optical density of the treated sample compared with the optical density of the control.

Bleomycin (BLEC), carboplatin (CDDP), 5-fluoruracil (5-FU), vincristine (VCR), epidoxorubicin (Epi-Dx) and methotrexate (MTX) were tested for comparison purposes.

L-aC was tested at the following concentrations: 0.2–2–20 mg/ml.

IC 50 concentrations of L-aC were attained within a range from 0.02 to 0.7 mg/ml, whereas IC 90 concentrations of L-aC were reached in a range from 0.7 to 20 mg/ml (Tables 1, 2, 3, 4, 5). The most active medicaments were L-aC (4/5), VCR (4/5), MTX (2/5), Epi-Dx (2/5), 5-FU (1/5).

The addition of somatostatin to L-aC at concentrations from 0.1 to 10 micrograms/ml surprisingly caused an about 10% increase in its therapeutical potential; in fact, in the tested case, particularly resistant to chemoantiblastics, the combination L-aC+somatostatin proved to be one of the three most active regimens.

The studies of point 4 evidence that L-aC has "in vitro" antitumour activity equal to or higher than that of other antitumour compounds, and anyway comparable to that of Vincristine, which is a substance having one of the most potent antiblastic effects known to day but also much more toxic than L-aC. Moreover, the combination of L-aC with somatostatin causes an about 10% increase in its therapeutical potential.

In vitro short-term chemosensitivity assay (according to Hill and coll.)

(Cell Vitality Percentage After Exposure to the Antitumoral)—Raw Data

TABLE 1

| concentration | 0 | 0.1x | 1x | 10x |
|---|---|---|---|---|
| VCR | 100 | 7.8 | 4.6 | 3.8 |
| CBP | 100 | 7.1 | 7 | 6.5 |
| Epi-Dx | 100 | 14 | 7.8 | 4.8 |
| 5-FU | 100 | 43 | 12 | 5.7 |
| MTX | 100 | 13.5 | 5 | 3.9 |
| LAC | 100 | 58 | 4.8 | 4 |

(Cells from Nasopharynx Carcinoma Explant)

TABLE 2

| concentrations | 0 | 0.1x | 1x | 10x |
|---|---|---|---|---|
| VCR | 100 | 70 | 45 | 11 |
| CBP | 100 | 78 | 58 | 34 |
| Epi-Dx | 100 | 59 | 21 | 7 |
| 5-FU | 100 | 53 | 38 | 13 |
| BLM | 100 | 55 | 36 | 17 |
| LAC | 100 | 62 | 32 | 15 |
| Lac + Som | 100 | 55 | 27 | 13 |

(Cells from Larynx Carcinoma Explant)

TABLE 3

| concentrations | 0 | 0.1x | 1x | 10x |
|---|---|---|---|---|
| VCR | 100 | 32 | 19 | 4.8 |
| CBP | 100 | 88 | 50 | 21 |
| Epi-DX | 100 | 57 | 32 | 16 |
| 5-FU | 100 | 52 | 45 | 23 |
| BLM | 100 | 81 | 68 | 34 |
| LAC | 100 | 42 | 24 | 7.2 |

(Cells from Larynx Carcinoma Explant)

TABLE 4

| concentrations | 0 | 0.1x | 1x | 10x |
|---|---|---|---|---|
| VCR | 100 | 1.9 | 1.3 | 1.3 |
| MTX | 100 | 18 | 4 | 3.1 |
| Epi-Dx | 100 | 16 | 8 | 8 |
| 5-FU | 100 | 40 | 14 | 14 |
| BLM | 100 | 82 | 79 | 62 |
| LAC | 100 | 3.8 | 1.5 | 1.4 |

(Cells from Larynx Carcinoma Explant)

TABLE 5

| concentrations | 0 | 0.1x | 1x | 10x |
|---|---|---|---|---|
| VCR | 100 | 23 | 4.2 | 2 |
| CBP | 100 | 72 | 53 | 45 |
| Epi-Dx | 100 | 60 | 21 | 18 |
| 5-FU | 100 | 55 | 13 | 8.2 |
| BLM | 100 | 60 | 35 | 31 |
| LAC | 100 | 63 | 37 | 32 |

(Cells from Larynx Carcinoma Explant)

5. Effects of L-aC on Sprague-Dowley Rats Inoculated with Yoshida Ascitogenic Tumour.

Yoshida tumour is a transplantable, ascitogenic experimental tumour consisting of histiocyte-like immortalized cells.

The tumour causes, on the average 7 days after the intraperitoneal inoculation in Sprague-Dowley rat, the formation of 120–150 ml of ascites which reappears 3–4 days after complete emptying of the peritoneal cavity and induces death of all the animals within 14–16 days after inoculation.

Treatment

300 Sprague-Dowley rats (4 months old, mean weight: 200 g), under standard feeding and temperature conditions (25° C.), were inoculated with Yoshida tumour. The onset and evolution of the tumour were checked by daily observation and weighing. One week after the inoculation of the tumour, rats were divided in 6 groups and treated as follows:

Group 1: 50 rats were subjected, on day 8 to 14, to daily emptying of 5 ml of ascitic fluid which was substituted with 5 ml of saline solution;

Group 2: 50 rats were subjected, on day 8 to 14, to daily emptying of 5 ml of ascitic fluid which was substituted with 50 mg of L-aC diluted in 5 ml of saline solution;

Group 3: 25 rats were subjected, on day 8 to 14, to daily emptying of 5 ml of ascitic fluid which was substituted with 80 mg of L-aC diluted in 5 ml of saline solution;

Group 4: 25 rats were subjected, on day 8 to 14, to daily emptying of 5 ml of ascitic fluid which was substituted with 120 mg of L-aC diluted in 5 ml of saline solution;

Group 5: 100 rats were subjected, on day 8 to 14, to evacuation on alternate days of 5 ml of ascitic fluid which was substituted with 25 mg of L-aC diluted in 5 ml of saline solution;

Group 6: 50 rats were used as control and received no treatment.

Results

All of the 50 animals of group 1 died within day 14 after inoculation of the tumour.

All of the 50 animals of group 2 died within day 14 after inoculation of the tumour.

All of the 25 animals of group 3 died within the first 72 hours after the 1st administration of the substance i.e. within day 10 after inoculation of the tumour.

All of the 25 animals of group 4 died within the first 24 hours from the 1st administration of the substance, i.e. within day 8 after inoculation of the tumour.

Of the 100 animals of group 5, 47 were still alive on day 15 after inoculation of the tumour and showed a remarkable reduction of the ascites amount.

The 50 animals of group 6 died within day 14 after inoculation of the tumour.

The 47 survived animals, all belonging to group 5, received the treatment for a further 2 weeks. Of said animals, 21 died during the treatment, whereas 26 were still alive on day 28 after inoculation of the tumour and showed a complete disappearance of the ascitic fluid. The animals appeared in good health, regularly fed and had glossy, thick coat, lively motory activity and normal sexual activity.

In order to evaluate any residual neoplasms, the survived animals were observed for a further 6 weeks during which no deaths occurred. At the end of the observation, 6 animals were sacrified and necroscopy detected no presence of the disease. More specifically, no ascites was evidenced and no tumour cells could be detected after peritoneal washing with saline solution.

The studies of point 5 evidence that L-aC has a potent "in vivo" antitumour activity, comparable to that exerted "in vitro", at doses inducing plasmatic concentrations comparable to the concentrations used "in vitro".

| Mortality curves in Sprague Dowley rats transplanted with Yoshida tumour and treated with different dosages of 1-acetyl-Carnitine intraperitoneally | | | | | | |
|---|---|---|---|---|---|---|
| Group 1 | Group 2 | Group 3 | Group 4 | Group 5 | Group 6 | Days |
| 50 | 50 | 25 | 25 | 100 | 50 | 0 transplant |
| 50 | 50 | 25 | 25 | 100 | 50 | 1 |
| 50 | 50 | 25 | 25 | 100 | 50 | 2 |
| 50 | 50 | 25 | 25 | 100 | 50 | 3 |
| 50 | 50 | 25 | 25 | 100 | 50 | 4 |
| 50 | 50 | 25 | 25 | 100 | 50 | 5 |
| 50 | 50 | 25 | 25 | 100 | 50 | 6 |
| 50 | 50 | 25 | 25 | 96 | 50 | 7 |
| 41 | 42 | 12 | 0 | 91 | 42 | 8 |
| 36 | 32 | 5 | | 83 | 31 | 9 |
| 22 | 21 | 0 | | 79 | 23 | 10 |
| 19 | 17 | | | 61 | 15 | 11 |
| 10 | 12 | | | 50 | 8 | 12 |
| 3 | 5 | | | 48 | 4 | 13 |
| 0 | 0 | | | 47 | 0 | 14 |
| saline | 50 mg lac | 80 mg lac | 120 mg lac | 25 mg lac | blank | |

6. Effects of L-aC on the Survived Sprague-Dowley Rats Reinoculated with Yoshida Tumour 20 survivors rats previously transplanted with Yoshida tumour and subjected to the treatment on alternate days with 25 mg of L-aC diluted in 5 ml of saline solution for 4 weeks, were reinoculated with the tumour, at the end of the 6 week observation period.

Until day 14 after reinoculation, no animals showed ascites. Reinoculation was repeated one more time, again unsuccessfully.

The studies of point 6 evidence that L-aC, has an "in vivo" activity capable of inhibiting the thriving of the tumour, which suggests the possibility to use the substance in antitumour chemoprevention protocols.

7. Chemopreventive Effects of L-aC Treatment on Sprague-Dowley Rats Yoshida Tumour Inoculation and Thriving.

In order to elucidate the actual chemoprevention antitumour Potentialities of L-aC, 125 Sprague-Dowley rats (4 months old, mean weight: 200 g), under standard feeding and temperature conditions (25° C.), were divided in 5 groups and treated as follows:

Group 1: 25 rats were intraperitoneally treated, on alternate days for 10 days, with 25 mg of L-aC diluted in 5 ml of saline solution. On day 10 they were inoculated with Yoshida tumour.

Group 2: 25 rats were intraperitoneally treated, on alternate days for 10 days, with 25 mg of L-aC diluted in 5 ml of saline solution. On day 10 they were inoculated with Yoshida tumour. Starting from day 11, they were further treated intraperitoneally, on alternate days, with 25 mg of L-aC diluted in 5 ml of saline solution, for a further 10 days.

Group 3: 25 previously untreated rats were inoculated, on day 10, with Yoshida tumour. Starting from day 14 they were intraperitoneally treated, on alternate days, with 25 mg of L-aC diluted in 5 ml of saline solution for 10 days.

Group 4: 25 previously untreated rats were inoculated on day 10 with Yoshida tumour. On day 18 to 24 they were intraperitoneally treated, on alternate days, with 25 mg of L-aC diluted in 5 ml of saline solution for 10 days.

Group 5: 25 previously untreated rats were inoculated on day 10 with Yoshida tumour. On day 18 to 24 they were subjected to emptying, on alternate days, of 5 ml of ascitic fluid which was substituted with 50 mg of L-aC diluted in 5 ml of saline solution.

The onset and evolution of the tumour were checked by daily observation and weighing.

Results

In group 1, only 4/25 animals showed ascites on day 18 of observation, day 8 after tumour inoculation. They died within day 26 of observation, day 16 after tumour inoculation.

Of the 21 "ascites-free" animals, 13 appeared free from the disease and were still alive at day 27 of observation, day 17 after tumour inoculation whereas in the remaining 8 ascites, at first not evident, developed although late, and all animals died within day 27 of observation.

In group 2, only 5/25 animals showed ascites on day 18 of observation, day 8 after tumour inoculation. The 20 "ascitis-free" animals were removed from the group and observed separately. Of them, 3 were still alive on day 27 of observation, day 17 after tumour inoculation and showed markedly low or even no ascites amount.

Of the 20 "ascites-free" animals, 18 appeared free from the disease and still alive on day 27 of observation, day 17 after tumour inoculation whereas in the remaining 2 ascites, at first not evident, developed although late, and all animals died within day 27 of observation.

In group 3, 16/25 animals were still alive on day 27 of observation, day 17 after tumour inoculation and showed markedly low or even no ascites amount.

In group 4, 11/25 animals were still alive on day 27 of observation, day 17 after tumour inoculation and showed markedly low or even no ascites amount.

In group 5, all the animals died within day 26 of observation, day 16 after tumour inoculation.

Before treatment with L-aC, patients had undergone an individual number of endoscopic resections (Turb), varying from 6 to 19 and in 1 case partial cystectomy with ureterocystoneostomy had been performed.

In all patients, treatment with L-aC started immediately after endoscopic resection.

Patients were subjected to quarterly endoscopic verification for the first year from the beginning of the treatment.

Already at the first control, all patients were negative for the tumour and remained negative in the subsequent controls.

After 4 negative quarterly controls, the endoscopic control was performed every six months for a duration of 2 years.

To day, 2 patients have completed the follow-up and appear free from the disease whereas 6 are still under study but they also prove to be free from the disease.

The two remaining patients dropped out of the study as they moved to another town, but at the moment of the dropping-out they appeared free from the disease.

Neither significant changes in the hematochemical parameters nor side effects of any kind were observed during the treatment.

The studies of point 8 evidence that L-aC has "in vivo" activity capable of controlling tumour relapse in resected carcinoma patients, causing no toxic effects, even in case of long-lasting treatments or in elderly patients.

In brief, the studies up-to-now carried out prove that:

1: L-aC "in vitro" at a concentration of 20 mg/ml, is capable of impacting on the cell cycle of tumour cells, inducing a marked block in $G_1$, thus remarkably inhibiting cell replication and tumour progression.

|  | 01 | 03 | 05 | 07 | 09 | 10 | 11 | 14 | 18 | 21 | 24 | 27 | 30 | 45 |
|---|---|---|---|---|---|---|---|---|---|---|---|---|---|---|
|  |  |  |  |  |  |  | Yosh |  |  |  |  |  |  |  |
| Group 1 | 25 | 25 | 25 | 25 | 25 | 25 | 25 | 25 | 25 | 20 | 15 | 13 | 13 | 13 |
| Group 2 | 25 | 25 | 25 | 25 | 25 | 25 | 25 | 25 | 25 | 21 | 21 | 21 | 21 | 21 |
| Group 3 | 25 | 25 | 25 | 25 | 25 | 25 | 25 | 25 | 25 | 20 | 18 | 16 | 16 | 16 |
| Group 4 | 25 | 25 | 25 | 25 | 25 | 25 | 25 | 25 | 25 | 15 | 13 | 11 | 11 | 11 |
| Group 5 | 25 | 25 | 25 | 25 | 25 | 25 | 25 | 25 | 25 | 8 | 3 | 0 | 0 | 0 |

On day 45 of observation, the surviving animals appeared in good health, regularly fed and had glossy, thick coat, lively motory activity and normal sexual activity.

In order to evaluate any residual neoplasms, the survived animals were observed for a further 6 weeks during which no deaths occurred. At the end of the observation, 6 animals were sacrified and necroscopy detected no presence of the disease. More specifically, no ascites was evidenced and no tumour cells could be detected after peritoneal washing with saline solution.

The above results not only bear out that L-aC has strong "in vivo" antitumour activity, comparable to that exerted "in vitro" and at doses inducing plasmatic concentrations comparable to the concentrations used "in vitro", but also that L-aC has "in vivo" activity capable of inhibiting the thriving of the tumour, which suggests the possibility to use the substance in antitumour chemoprevention protocols.

8. Effects of L-aC on Patients with Urinary Bladder Multirecurrent Neoplasia 10 patients, 8 males and 2 females, of age from 55 to 75 years, all affected with multirecurrent urinary bladder neoplasia, at stages ranging from pT1G1NxMx and pT2G3NxMx, were orally treated with L-aC, at a standard dosage of 2 g/day, for a time from 10 to 12 months. They were then subjected to follow-up ranging from 6 to 22 months.

2: L-aC has "in vitro" antitumour activity equal to or higher than that of other antitumour compounds, and anyway comparable to that of Vincristine, which is a substance having one of the most potent antiblastic effects known to day but is also much more toxic than L-aC.

3: L-aC added to somatostatin increases its antitumour therapeutical potential by about 10%.

4: L-aC has "in vivo" a strong antitumour activity comparable to that exerted "in vitro", at doses inducing plasmatic concentrations comparable to the concentrations used "in vitro".

5: L-aC has an "in vivo" activity capable of inhibiting the thriving of the tumour, which suggests the possibility to use the substance in chemoprevention antitumour protocols.

6: L-aC has "in vivo" activity capable of controlling tumour relapse in resected carcinoma patients, causing no toxic effects, even in case of long-lasting treatments or in elderly patients.

The antitumour compositions according to the invention can be formulated in pharmaceutical forms which can be administered through the oral (for example tablets, capsules, sachets) or parenteral route (for example vials for intramuscular or intravenous injection or for intraperitoneal administration), in unitary doses ranging from 0.5 to 5 g of acylcarnitine, for example L-acetylcarnitine, optionally in combination with other antitumour medicaments at the suitable dosages. More particularly, the compositions of the invention can contain a combination of L-acetylcarnitine and somatostatin, which can be administered at dosages of 1–5 g/day of L-acetylcarnitine, or even higher, depending on the physician's opinion.

What is claimed is:

1. A method for inhibiting tumors in a patient, comprising:
    administering to said patient an effective amount of a composition comprising acylcarnitine optionally with somatostatin, wherein said effective amount inhibits tumors in said patient, said composition is administered by the oral, intramuscular, intravenous or intraperitoneal routes, and said acylcarnitine is L-acetylcarnitine.

2. The method according to claim 1, wherein said acylcarnitine is administered in an amount of 0.2 to 20 mg/ml.

3. The method according to claim 1, wherein the acylcarnitine is L-acetylcarnitine hydrochloride.

4. The method according to claim 1, wherein said compound is administered by the oral route.

* * * * *